United States Patent
Suga et al.

Patent Number: 5,120,965
Date of Patent: Jun. 9, 1992

[54] APPARATUS AND METHOD FOR INVERSE PHOTOEMISSION

[75] Inventors: Shigemasa Suga, Osaka; Hirohumi Namatame, Tokyo, both of Japan

[73] Assignee: Shimadzu Corporation, Kyoto, Japan

[21] Appl. No.: 756,659

[22] Filed: Sep. 9, 1991

[30] Foreign Application Priority Data

Sep. 10, 1990 [JP] Japan .................... 2-240508

[51] Int. Cl.⁵ .................... G01N 23/22; G01N 21/62
[52] U.S. Cl. .................... 250/372; 250/458.1; 250/459.1
[58] Field of Search ............ 250/372, 306, 458.1, 250/459.1

[56] References Cited

U.S. PATENT DOCUMENTS 4,472,634  9/1984  Baptist et al. .............. 250/372
4,871,915  10/1989  Prince ........................ 250/372

OTHER PUBLICATIONS

Schafer et al., "Bandpass Photon Detector with High Efficiency for Inverse Photoemission", Rev. Sci. Instrum. 58 (4), Apr. 1987-American Institute of Physics, pp. 710-711.

Suga et al., "Inverse Photoemission Spectroscopy", Journal of the Specroscopical Society of Japan (Bunkyo Kenkyu), vol. 39, No. 1 (1990), pp. 2-18.

Primary Examiner—Carolyn E. Fields
Attorney, Agent, or Firm—Armstrong, Nikaido, Marmelstein, Kubovcik, and Murray

[57] ABSTRACT

Disclosed is an apparatus for inverse photoemission spectroscopy in which optical filters having at least two different cutoff energies are selectively provided in the optical path of a vacuum ultraviolet-ray detector. The bandpass characteristic of emitted light obtained by causing monochromatic energy to impinge upon a sample is obtained by different high cutoff energies of the two filters. The different high cutoff energies are set by selection of different types of ionic crystals and the temperature characteristic of the same or different types of ionic crystals.

10 Claims, 8 Drawing Sheets

APPARATUS AND METHOD FOR INVERSE PHOTOEMISSION

BACKGROUND OF THE INVENTION

This invention relates to a measurement apparatus and method for determining the electronic state of a substance.

Photoemission spectroscopy is well known as a method of determining the electronic state of a substance. In photoemission spectroscopy, external light is made to impinge upon a sample and the kinetic energy, momentum, electron spin, etc., of electrons emitted by the sample are measured. This method is suited mainly for investigating occupied electronic states.

As a method of investigating unoccupied electronic states, a method of detecting light or an electron beam from the occupied state by excitation is known. With this method, however, it is difficult to independently obtain information relating to the unoccupied state owing to the influence of the density of the coupling states of the occupied and unoccupied electronic states and the Coulomb interactions between electrons and positive holes. Inverse photoemission spectroscopy has appeared in recent years and is an effective expedient for investigating unoccupied electronic states.

The following phenomenon is utilized in inverse photoemission spectroscopy: When an electron beam of monochromatic energy Ei impinges upon a sample from the outside (vacuum), the electron beam undergoes an electric dipole transition to an unoccupied electronic state of lower energy. Light is emitted at such time. By measuring the emitted light, the unoccupied electronic state can be determined.

Two types of measurement apparatus are known for practicing this inverse photoemission spectroscopy. One type of apparatus is so adapted that the emission strength of light having a constant energy of hv is measured as a function of the energy Ei of the incident electron beam. The apparatus of this type employs a bandpass-type photodetector. The second type of apparatus is of the spectroscope type and is adapted to measure an emission spectrum distribution of the energy Ei of each incident electron.

Known examples of detectors for use in the first type of measurement apparatus include a detector which employs a Geiger-Müller counter, and a detector which is a combination of a Cu-BeO photomultiplier and a $CaF_2$ or $SrF_2$ entrance window.

The bandpass filter used in the detector which employs the Geiger-Müller counter comprises a combination of an entrance window and a gas. The entrance window, which consists of $CaF_2$, for example, absorbs and cuts off light having a short wavelength. An example of the gas is $I_2$ gas, which is used as an ionized gas (which may be mixed with a rare gas serving as a quench gas). The gas is for cutting off light in the long-wavelength region.

A detector which is a combination of a Cu-BeO photomultiplier and a $CaF_2$ or $SrF_2$ entrance window is described in *Rev. Sci. Instrum.*, 58, 710, published in 1987 by I. Schäfer, W. Drube, M. Schlüter, G. Plagemann and M. Skibowski, and in the *Journal of the Spectroscopical Society of Japan* (Bunko Kenkyu), Vol. 39, No. 1, P. 6, published in 1990 by Shigemasa Suga, Hirofumi Namatake, Susumu Ogawa and Toyohiko Kinoshita.

This detector is constructed by providing, in the order mentioned, a light shield, an entrance window consisting of $CaF_2$ or $SrF_2$ and an electric-field shielding mesh in front of a Cu-BeO photomuliplier.

The bandpass characteristic of this detector is decided by the characteristics of the Cu-BeO photomuliplier and the characteristics of entrance window. The low-energy cutoff region of the bandpass characteristic is obtained by the first transition of the Cu-BeO photomultiplier sensitivity and cuts off long wavelengths. By way of example, the aforementioned sensitivity exhibits a characteristic which starts to rise from the vicinity of 7 eV and rises sharply in the neighborhood of from 8 eV to 9 eV.

On the other hand, the high-energy cutoff region of the bandpass characteristic is obtained by the sharp absorption edge of the entrance window and cuts off short wavelengths. By way of example, the absorption edges of $CaF_2$ and $SrF_2$ are 10 eV and 9.8 eV, respectively.

By combining these two, the peak of the bandpass characteristic appears in the vicinity of 9.8 eV and 9.4 eV.

The above-mentioned detector is disadvantageous in that it has a resolution of only 0.6 to 0.3 eV and possesses a low-energy cutoff characteristic which does not exhibit a steep rise. In addition, the limit on the full half-width of the bandpass characteristic is 0.3 eV. The reason for the foregoing is that low-energy cutoff is performed using the photoelectric emission threshold values of the gas and Cu-BeO.

SUMMARY OF THE INVENTION

An object of the present invention is to provide an apparatus and method for inverse photoemission spectroscopy in which high energy resolution (0.1 eV) can be obtained.

Another object of the present invention is to provide a detecting apparatus having a bandpass filter which exhibits a sharp bandpass characteristic.

The present invention solves the aforementioned problems and provides an apparatus and method for determining the electronic state of a substance by high energy resolution. In the present invention, an electron beam is applied to a sample, light emitted from the sample is directed through optical filters having different high-energy cutoff regions, and the emission strength of energy of a constant hv possessed by the emitted light, which is obtained via the optical filters, is measured from the differential between two outputs of a photodetector.

Other features and advantages of the present invention will be apparent from the following description taken in conjunction with the accompanying drawings, in which like reference characters designate the same, or similar parts throughout the figures thereof.

DESCRIPTION OF THE PREFERRED EMBODIMENTS

The principle of inverse photoemission spectroscopy is as follows: When electrons having an electron energy represented by $E_i$ impinge upon the interior of a crystal, an electric dipole transition occurs within the crystal, light possessing an energy of $h\nu = E_i - E_f$ is emitted and an electronic energy state represented by $E_f$ is attained. This electronic energy state of $E_f$ represents the unoccupied electronic state within the crystal. Accordingly, if the electronic energy $E_i$ of the incident electrons and the energy $h\nu$ of the emitted light are known, the unoccupied electronic state of the electrons can be found from the relation $E_f = E_i - h\nu$, where $E_i$ is obtained by measuring the electron energy incident upon the crystal, and $h\nu$ is obtained by measuring the emitted light. The measurement of light of a constant energy $h\nu$ can be performed using a bandpass filter of energy $h\nu$. The present invention provides a high-resolution bandpass filter for light of energy $h\nu$. This filter makes it possible to measure the unoccupied electronic state of electrons highly accurately.

The apparatus and method for inverse photoemission spectroscopy according to the present invention are realized by using ionic crystal filters having slightly different values of high-energy cutoff energy, and a vacuum ultraviolet ray detector for detecting the outputs of the filters.

Figure 2:
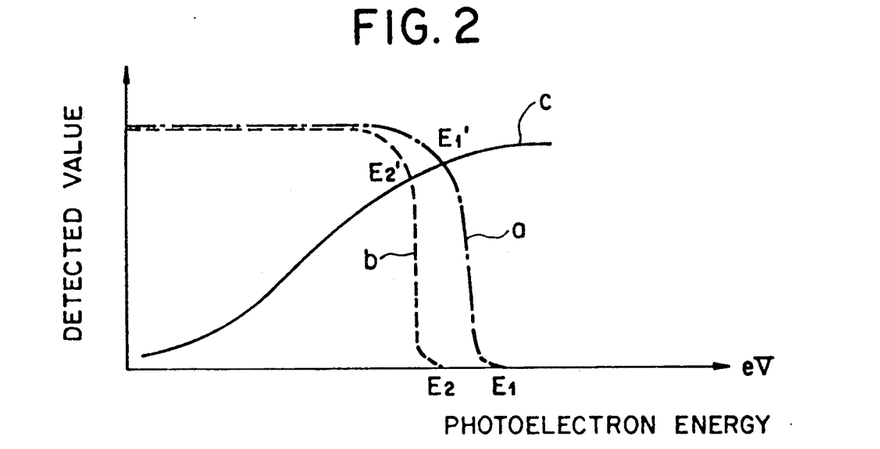
FIG. 2 is a diagram illustrating the bandpass characteristics of filters having different energy cutoffs according to the present invention.

FIG. 2 illustrates the photoelectron energy characteristics of ionic crystal filters. The one-dot chain line (a) indicates the characteristic defined by a high-energy cutoff energy $E_1$, and the dashed line (b) indicates the characteristic defined by a high-energy cutoff energy $E_2$, of two ionic crystal filters, with $E_1 > E_2$. The solid line (c) indicates the characteristic of a photodetector such as a photomultiplier. The overall characteristic of the photodetector through the filters is obtained by combining the solid line and the one-dot chain line or the dashed line. This characteristic is illustrated in FIG. 3.

Figure 3:
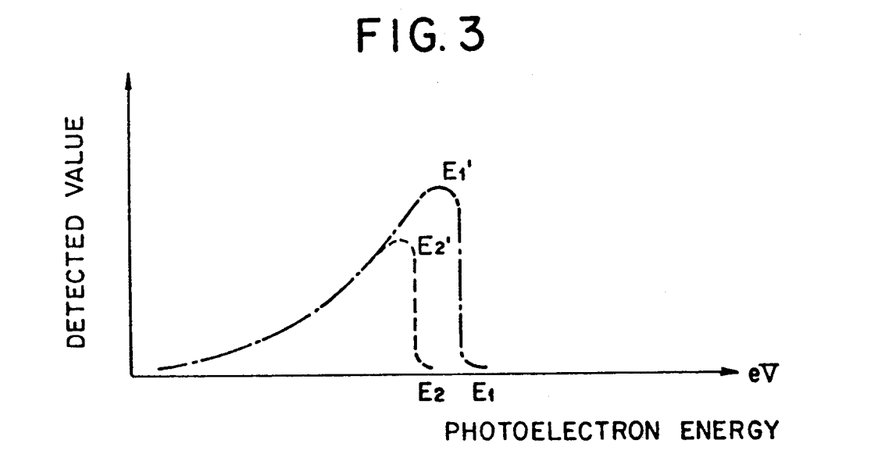
FIG. 3 is a diagram illustrating a bandpass characteristic based upon a filter-detector combination according to the present invention.

The characteristic curve indicated by the one-dot chain line or the dashed line in FIG. 3 represents the characteristic of the bandpass filter. As evident from FIG. 3, the characteristic of each bandpass filter is such that the first transition of the low cutoff energy is smooth, whereas the first transition of the high cutoff energy is steep. The smooth first transition derives from the characteristic of the photodetector, while the steep first transition results from the characteristic of the ionic crystal filter.

Figure 4:
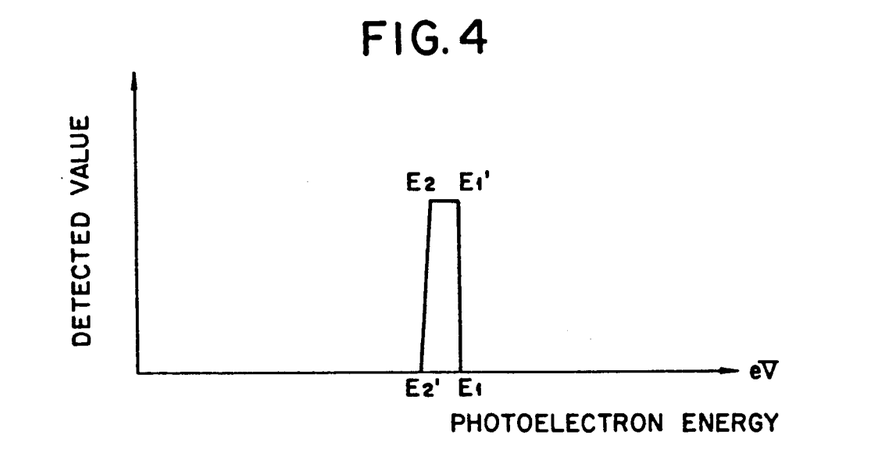
FIG. 4 is a diagram showing a bandpass characteristic of the inverse photoemission spectroscopic apparatus according to the present invention.

According to the present invention, the steep portions of the two ionic crystal filters are combined to construct a narrow half-width bandpass filter, having steep first and second transitions. The characteristic of this bandpass filter is schematically illustrated in FIG. 4. The energies of the peak values of the bandpass filter are $E_1'$ and $E_2'$.

The characteristic of the bandpass filter used in the present invention is decided solely by the high-energy cutoff energies of the ionic crystal filters and is unaffected by the characteristic of the photodetector. The ionic crystal filter having slightly different values of high energy cutoff energies used in the apparatus and method for inverse photoemission spectroscopy according to the present invention can be realized by an arrangement using two ionic crystals or an arrangement using one ionic crystal.

Figure 7:
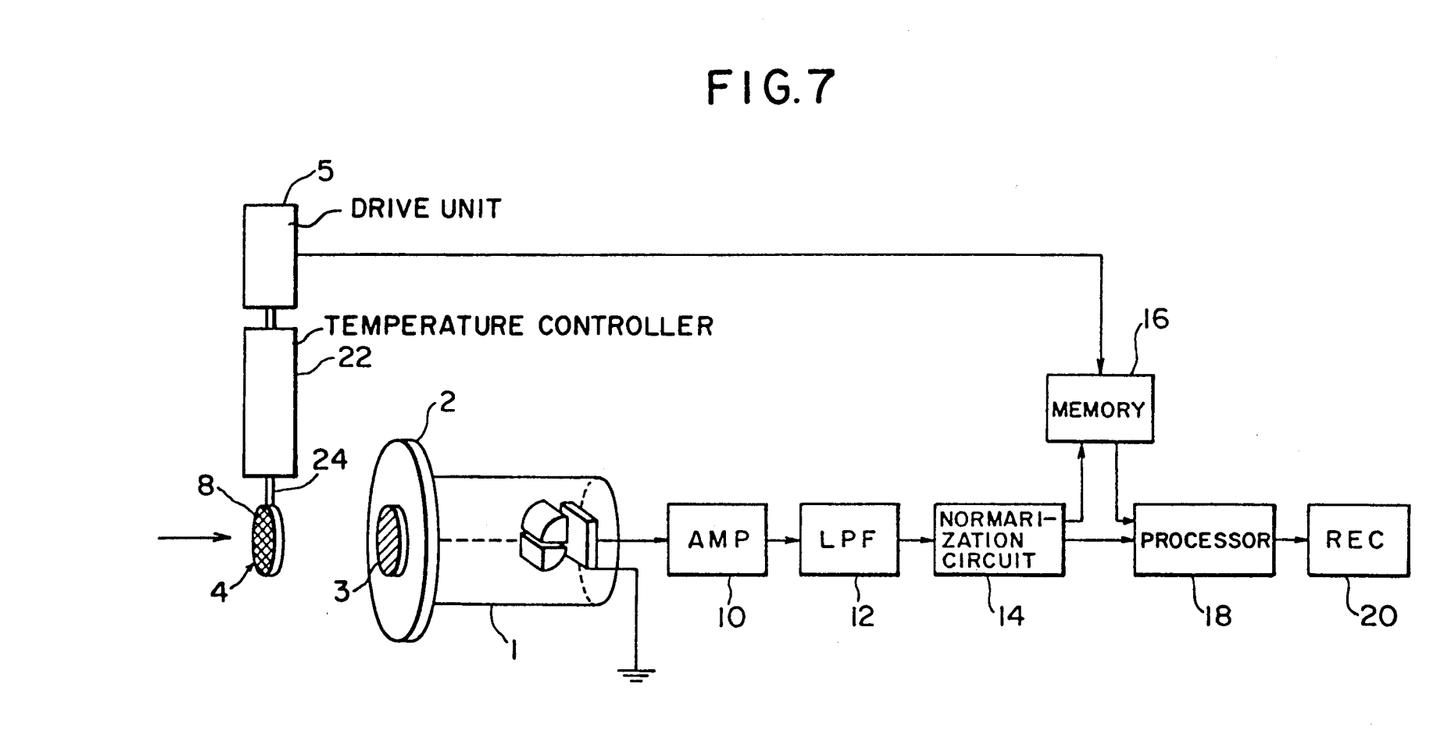
FIG. 7 is a schematic view of a fourth embodiment of the invention showing an inverse photoemission spectroscopic apparatus in which the energy cutoff characteristics of filters is changed.
Figure 8:
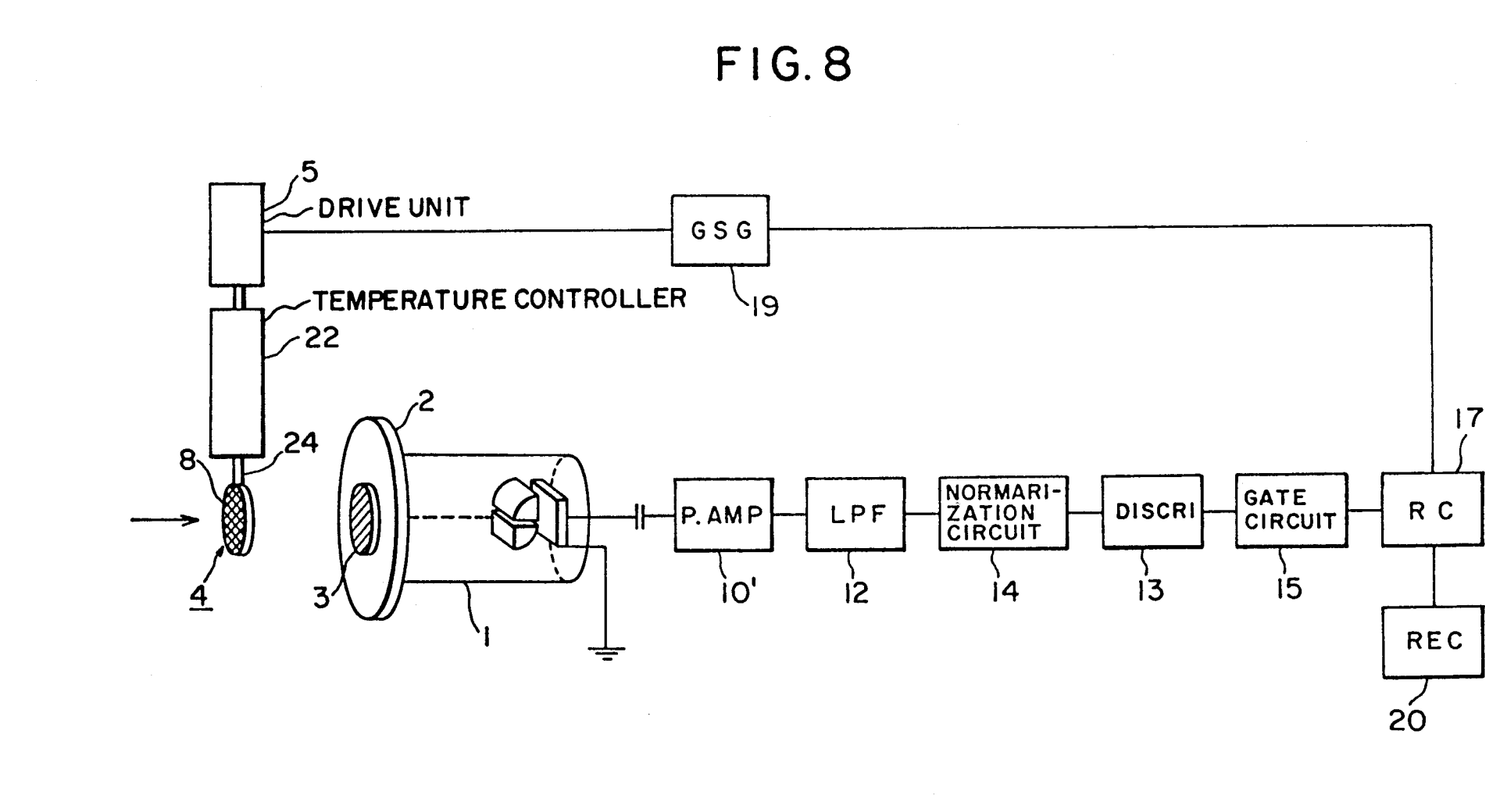
FIG. 8 is a schematic view of a fifth embodiment of the invention showing an inverse photoemission spectroscopic apparatus in which the energy cutoff characteristics of filters is changed.
Figure 9:
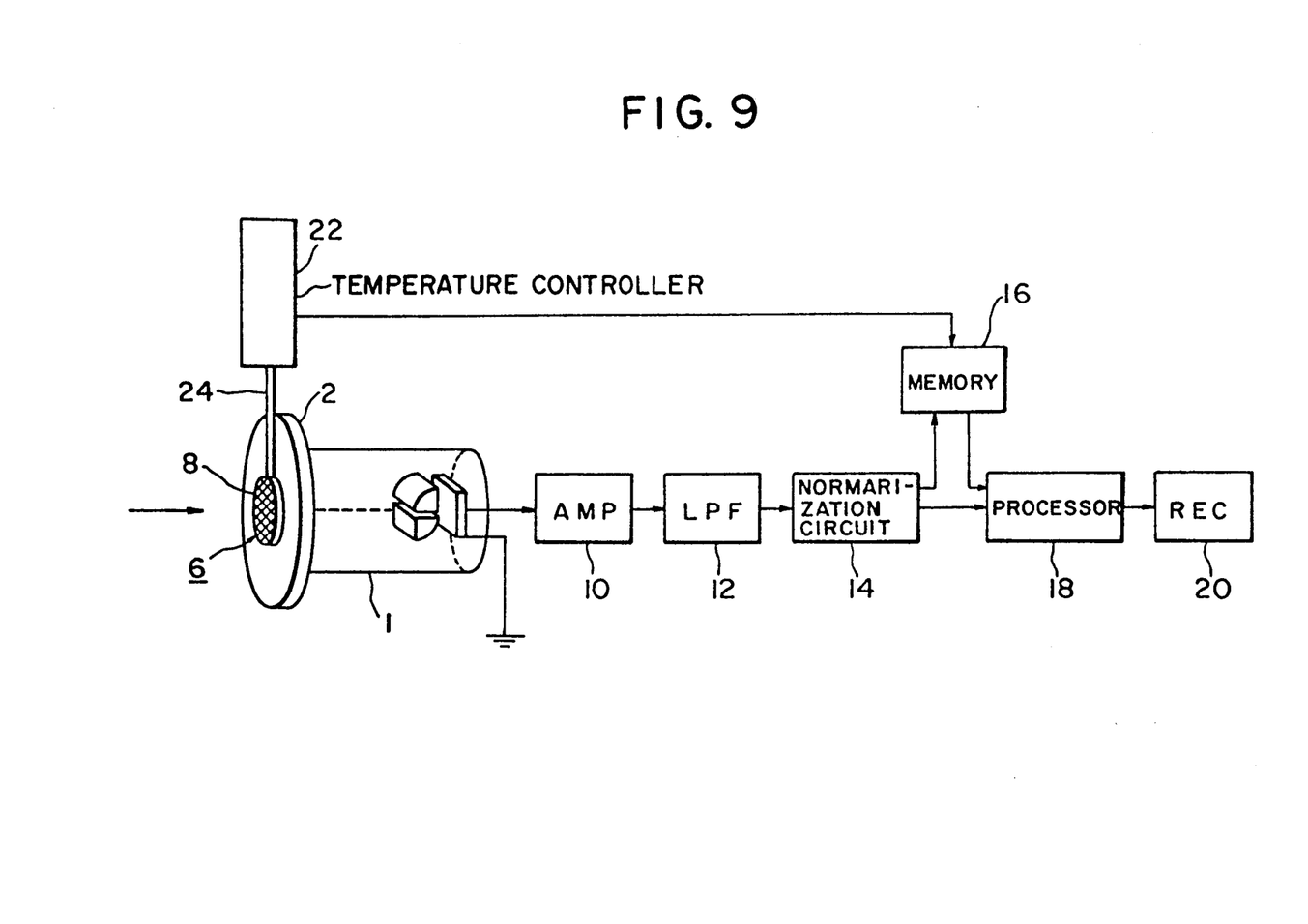
FIG. 9 is a schematic view of a sixth embodiment of the invention showing an inverse photoemission spectroscopic apparatus using one filter.
Figure 10:
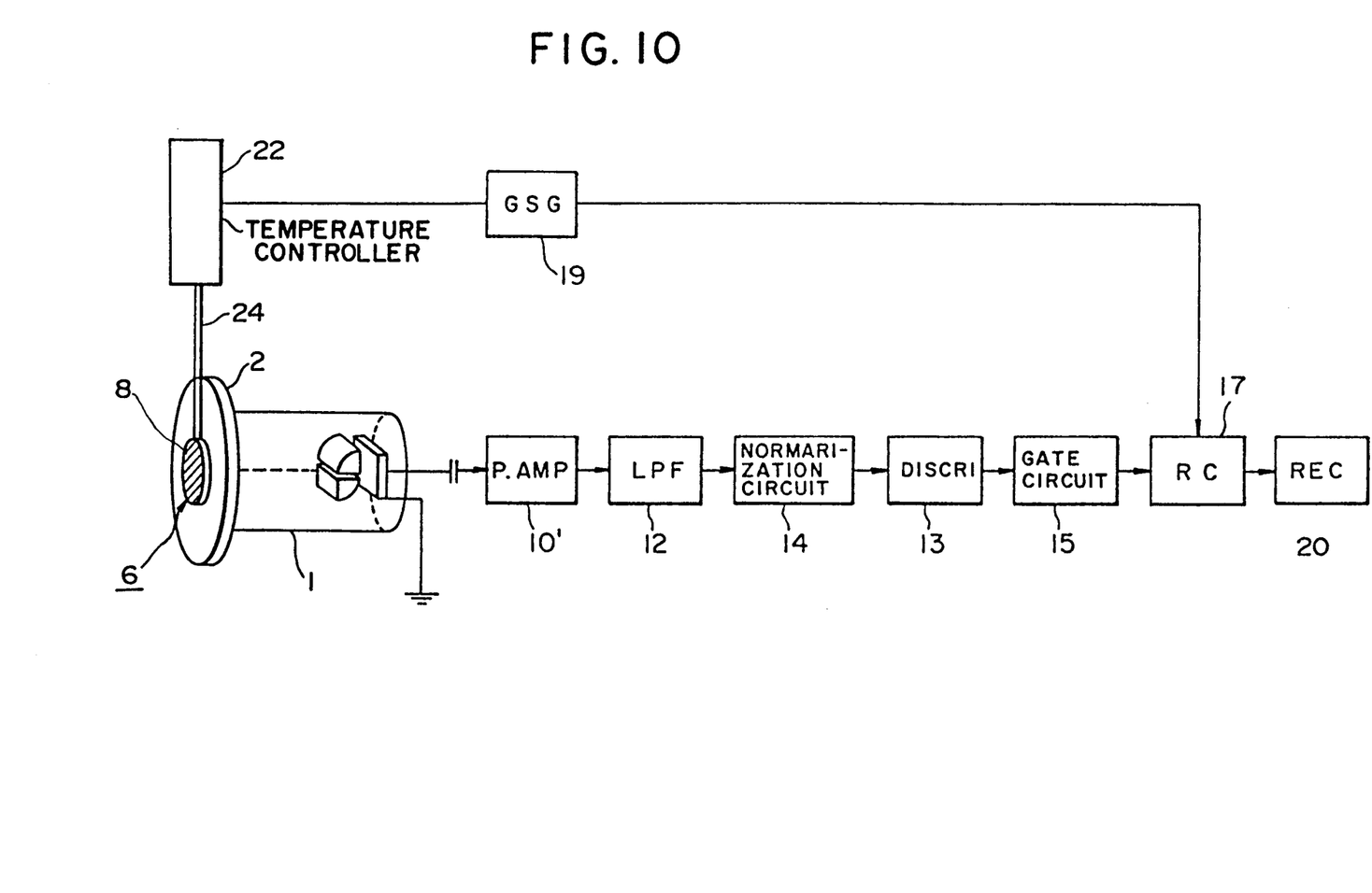
FIG. 10 is a schematic view of a seventh embodiment of the invention showing an inverse photoemission spectroscopic apparatus using one filter.

The embodiments shown in FIGS. 1, 5, 6, 7 and 8 are arrangements using two ionic crystals, and the embodiments shown in FIGS. 9 and 10 are arrangements using one ionic crystal.

Figure 1:
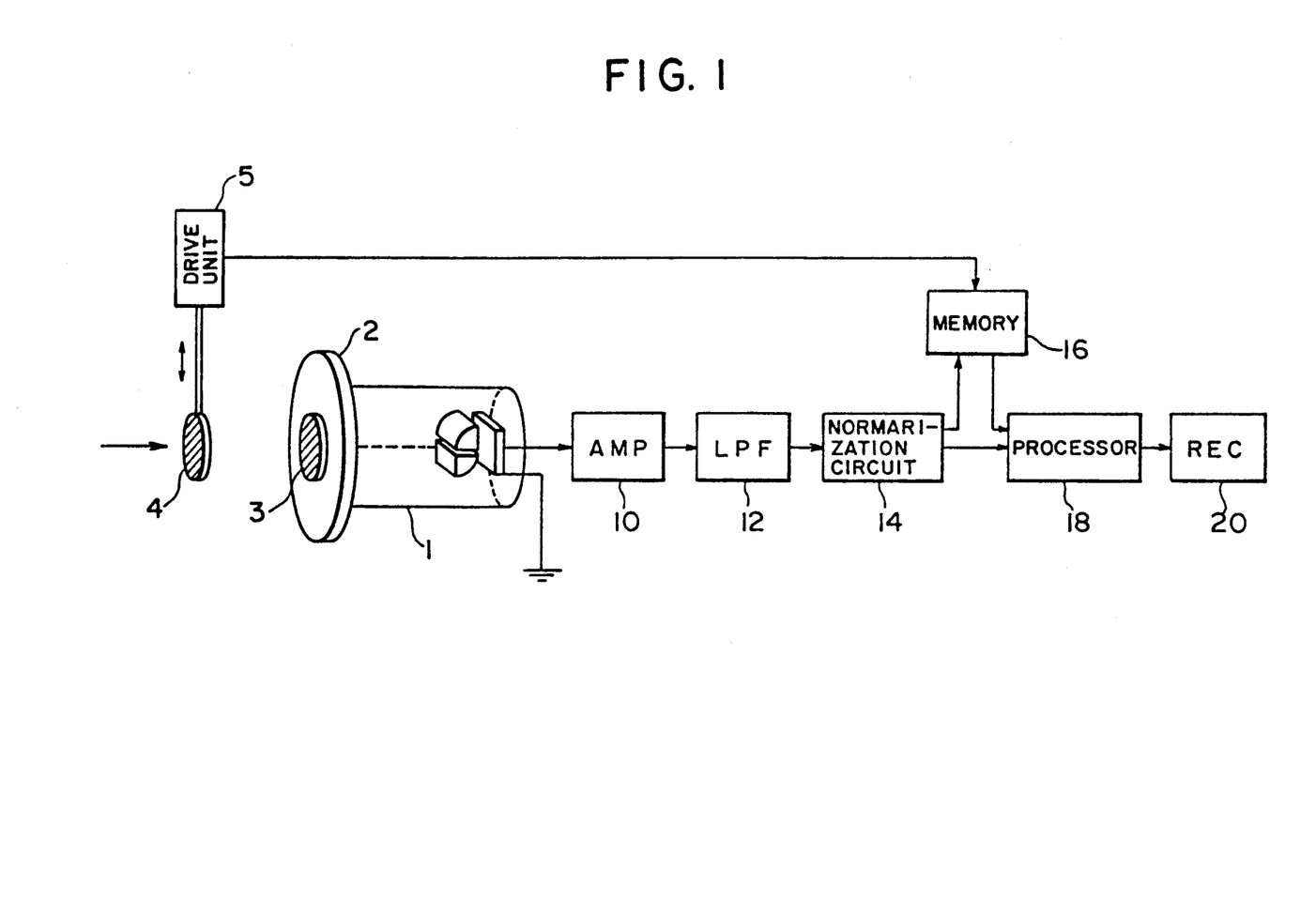
FIG. 1 is a schematic view showing an inverse photoemission spectroscopic apparatus illustrating a first embodiment of the present invention.

FIG. 1 illustrates a first embodiment of the present invention.

A filter 3 fixedly secured to a light shield 2 is provided on the light-incident side of a Cu-BeO photomultiplier 1. A filter 4 is arranged on the optical path in front of the filter 3. The cutoff energy $E_1$ of the filter 3 is larger than the cutoff energy $E_2$ of the filter 4 ($E_1 - E_2 = \Delta E$). The filters 3, 4 that are used are completely transparent at energies lower than the cutoff energy. If $CaF_2$ is used as filter 3 and $SrF_2$ as filter 4, then $\Delta E$ will be equal to 0.47 eV. The output of the photodetector 1 is fed into a memory 16 and a processor 18 via an amplifier (AMP) 10, a low-pass filter (LPF) 12 and a normalization circuit 14. The output of the memory 16 enters the processor 18. The output obtained from the processor 18 is recorded on a recorder (REC) 20. The memory 16 is realized by a register, a delay circuit and the like and is controlled in synchronization with a drive unit 5 which drives the filter 4.

A measurement method using the inverse photoemission spectroscopic apparatus shown in FIG. 1 will now be described.

The drive unit 5 is actuated to remove the filter 4 from the optical path, an electron beam of monochromatic energy is made to impinge upon a sample, and the light emitted from the sample is measured. The light impinges upon the photodetector 1 through the filter 3, the output of the photodetector 1 is amplified by the amplifier 10, and the amplified signal enters the normalization circuit via the low-pass filter 12. The signal is normalized in the normalization circuit 14 by the already measured reflectance and transmissivity of the filter. The output of the normalization circuit 14 enters the memory 16, where it is temporarily stored. The storage of this signal is controlled in synchronization with the drive unit 5.

Next, the drive unit 5 is actuated to place the filter 4 in the optical path so that the light impinges upon the photodetector 1 via the filters 3 and 4. The resulting output is applied directly to the processor 18 via the normalization circuit 14. At the same time, the output previously stored in the memory 16 and resulting from passage of light solely through the filter 3 is inputted to the processor 18. The processor 18 computes the differential between these two outputs to obtain $\Delta E$. The differential between the two results of normalized measurement is a spectrum measured at the bandpass characteristic of FIG. 4. By changing the energy Ei of the electron beam incident upon the sample, the emission strength of constant $h\nu$ can be measured as a function of the incident electron-beam energy Ei. The actual bandpass energy width is the result of adding $E_1-E_1'$, $[=(E_2-E_2')]$ to $\Delta E$. It is obvious that the signal applied to the memory 16 can be made the output obtained by passage of light through the filter 4.

Figure 5:
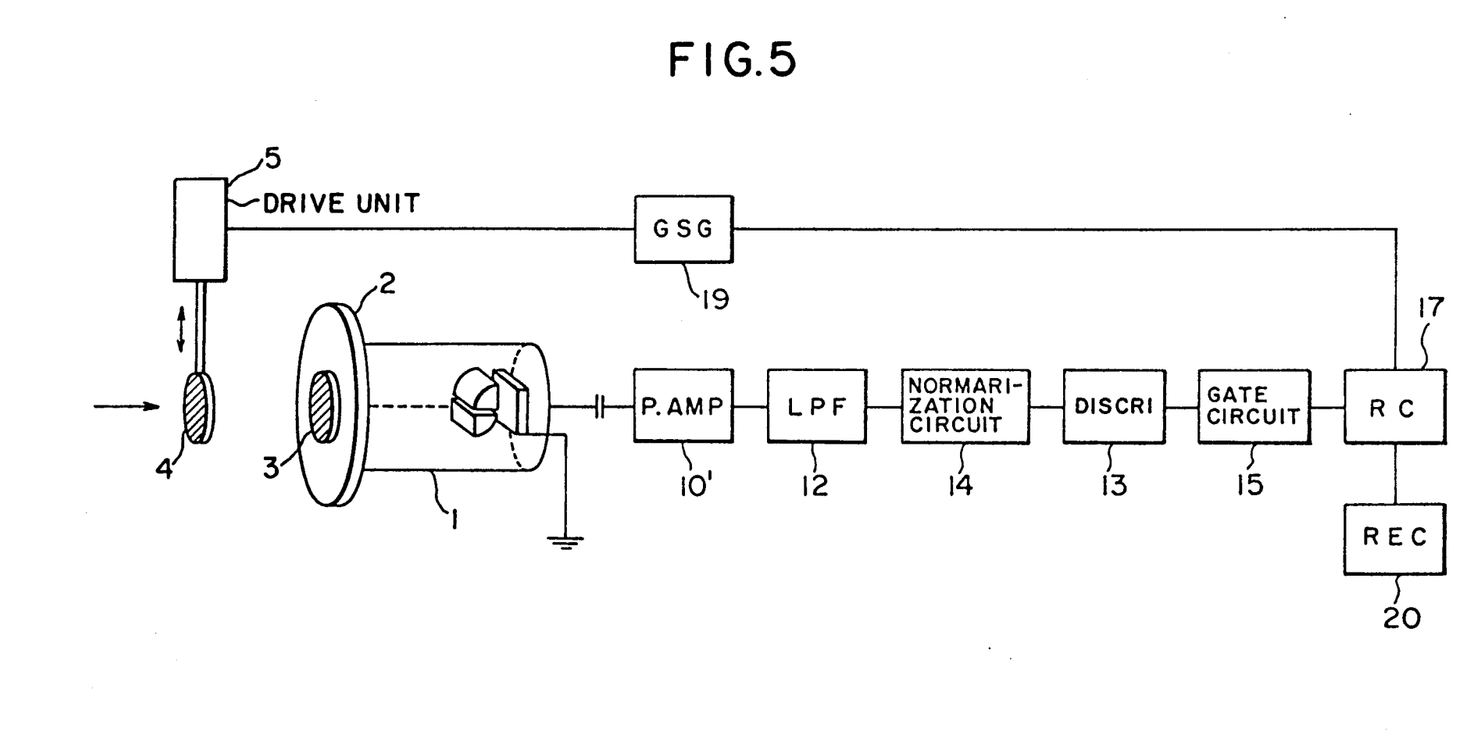
FIG. 5 is a schematic view showing an inverse photoemission spectroscopic apparatus which counts photoelectron pulses and is illustrative of a second embodiment of the present invention.

FIG. 5 illustrates a second embodiment of the present invention. The second embodiment is an arrangement in which the first embodiment shown in FIG. 1 is implemented in digital fashion.

In a case where the quantity of incident light is very small, it is convenient to employ a photoelectron counting method in which photoelectron pulses are counted as a digitized signal.

The output of the photodetector 1 enters a reversible counter (RC) 17 via a pulse amplifier (P.AMP) 10', the low-pass filter (LPF) 12, the normalization circuit 14, a pulse-height discriminator (DISCRI) 13 and a gate circuit 15. The reversible counter (RC) 17 is controlled via a gate signal generator (GSG) 19 by a synchronizing signal from the drive unit 5.

In the second embodiment, measurement is performed in the same manner as the first embodiment. The drive unit 5 is actuated to remove the filter 4 from the optical path, in which state photometry is performed. The pulse signal obtained by the pulse-height discriminator 13 is counted up in the reversible counter 17.

Next, photometry is carried out with the filter 4 placed in the optical path, and the pulse signal applied to the reversible counter 17 is counted down. A differential output represented by the count in the reversible counter 17 is obtained.

Figure 6:
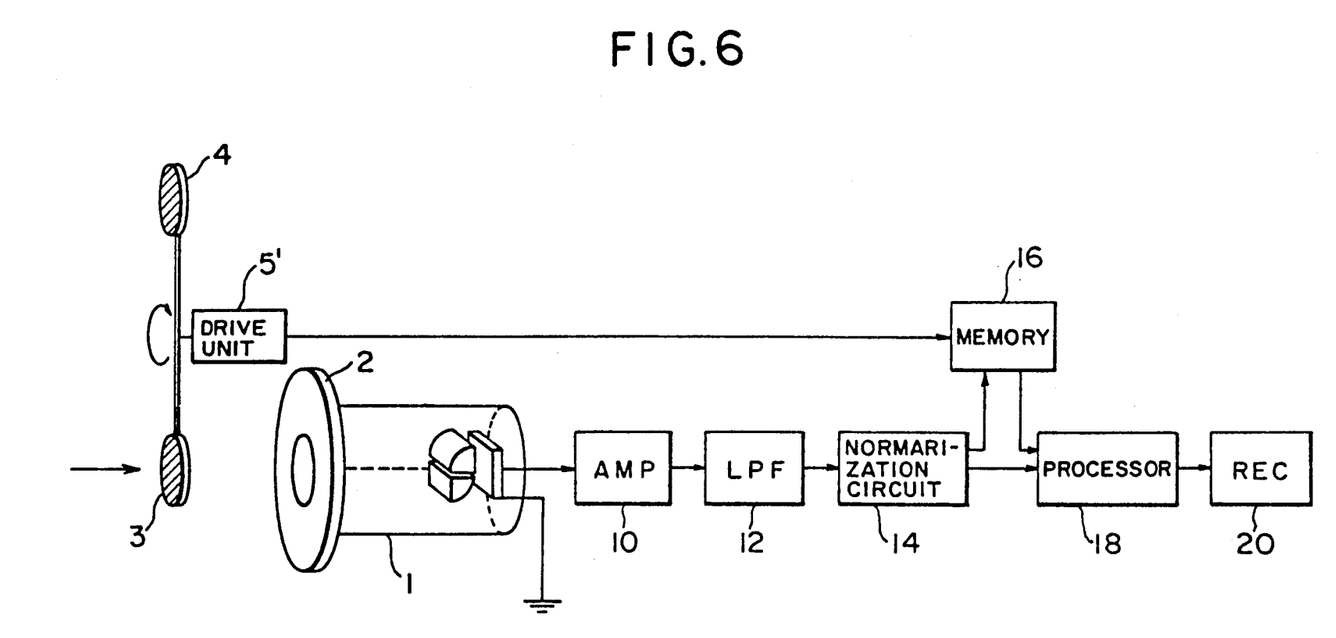
FIG. 6 is a schematic view of a third embodiment of the invention showing an inverse photoemission spectroscopic apparatus in which two filters are alternately arranged on an optical path.

A third embodiment of the present invention is depicted in FIG. 6.

In this embodiment, the light shield 2 provided on the light-incident side of the photodetector 1 is not furnished with a filter, unlike the first embodiment shown in FIG. 1. Instead, the filters 3 and 4 are capable of being revolved by a drive unit 5' so that they can be placed in the optical path selectively. When the filter 3 is placed in the optical path, the filter 4 is removed from the optical path. Conversely, when the filter 4 is placed in the optical path, the filter 3 is removed. The remaining components from the photodetector 1 onward are the same is in the embodiment of FIG. 1.

The operation of the third embodiment will now be described.

The drive unit 5' is actuated to place the filter 3 of cutoff energy $E_1$ in the optical path, an electron beam of monochromatic energy is made to impinge upon the sample, and the light emitted by the sample is measured.

The light is incident upon the photodetector 1 through the filter 3, and a normalized output is obtained via the amplifier 10, low-pass filter 12 and normalization circuit 14. This output is stored in the memory 16, which is controlled in synchronization with the drive unit 5'.

Next, the drive unit 5' is actuated to remove the filter 3 from the optical path and place the filter 4 of cutoff energy $E_2$ ($E_1>E_2$) in the optical path, after which measurement is performed in the same manner as described above. The normalized output from this measurement is inputted directly to the processor 18, which computes the differential between this output and that stored in the memory 16. It is obvious that can be performed in the same manner if the signal inputted to the memory 16 and the signal directly inputted to the processor 18 are interchanged.

FIG. 7 illustrates a fourth embodiment of the present invention.

This embodiment differs from the first embodiment shown in FIG. 1 in that a temperature controller 22 and a heat transfer member 24 are provided between the filter 4 and the drive unit 5. The temperature controller 22 is a heating system or a cooling system, and the heat transfer member 24 comprises a Cu block, a heat pipe, etc. The temperature controller 22 and the heat transfer member 24 are driven in unison by the drive unit 5. The filter 4 consists of a metal mesh 8 comprising Au, Cu or Ni provided on the surface of an ionic crystal. The metal mesh 8 is connected to the heat transfer member 24 so that the temperature of the ionic crystal constituting the filter 4 can be changed by controlling the temperature of the temperature controller 22.

The measurement method using this inverse photoemission spectroscopic apparatus is the same as that of the embodiment shown in FIG. 1. If $CaF_2$ at room temperature is used as the filter 3 and $CaF_2$ at room temperature $+50°$ C. is used as the filter 4, then $\Delta E$ will be equal to 0.065 eV. At normalization of the output obtained by measuring the light emission, it is necessary to perform a correction with regard to the transmissivity of the mesh.

Since the cutoff energy of the ionic crystal is temperature dependent, it is possible to select the value of the cutoff energy of the ionic crystal by controlling the temperature of the ionic crystal using the temperature controller.

A fifth embodiment of the present invention is shown in FIG. 8.

This embodiment is an arrangement in which the fourth embodiment shown in FIG. 7 is implemented in digital fashion. The digital signal processing is similar to that of the second embodiment illustrated in FIG. 5.

The filter 4 is connected to the temperature controller 22 via the heat transfer member 24. The movement of all of these components is controlled by the drive unit 5. The filter 4 is placed in the optical path and removed therefrom by the drive unit 5. The output of the photodetector 1 enters the reversible counter 17 via the pulse amplifier 10', low-pass filter 12, normalization circuit 14, height-discriminator 13 and gate 15. The reversible counter 17 is synchronized to the drive unit 5 via the gate signal generator 19.

The operation of the fifth embodiment will now be described.

An example in which 0.065 eV is obtained as $\Delta E$ using $CaF_2$ at room temperature as the filter 3 and $CaF_2$ at room temperature $+50°$ C. as the filter 4 will be described. The drive unit 5 is actuated to move the filter 4 in unison with the temperature controller 22 and heat transfer member 24, whereby the filter 4 is removed from the optical path. Under these conditions monochromatic energy electrons impinge upon the sample, and the light emitted from the sample is measured. The output of the photodetector 1 resulting from the light emission is directed through the pulse amplifier 10' and low-pass filter 12 and then enters the normalization circuit 14, which performs a correction of the filter characteristic. The output of the normalization circuit 14 is directed through the height-discriminator 13 and gate 15, and the output pulses are counted by the reversible counter 17. Next, the drive unit 5 is actuated to place the filter 4 in the optical path. The filter 4 is heated or cooled by the temperature controller 22 via the heat transfer member 24. Temperature control is carried out by the metal mesh 8 comprising Au, Cu or Ni on the surface of the filter 4. With the filter 4 thus placed in the optical path, the emitted light is measured and the reversible counter 17 is caused to count. At this time the drive signal from the drive unit 5 enters the reversible counter 17 via the gate signal generator 19, so that the counter is counted down. The differential output resulting from the two measurement operations is obtained from the count in counter 17.

Sixth and seventh embodiments of the present invention will be described with reference to FIGS. 9 and 10, respectively.

In these embodiments, the apparatus for inverse photoemission spectroscopy according to the present invention is realized using only one filter. Signal processing in the sixth embodiment is similar to that of the first embodiment. Only one filter 6 is provided on the light-incident side of the photodetector 1. The filter 6 is provided with a metal mesh 8, just as in the filter 4 of the fourth and fifth embodiments, and the filter 6 is connected to the temperature controller 22 via the heat transfer member 24.

The measurement method of inverse photoemission spectroscopy according to these embodiments will now be described.

First, the filter 6 is brought to room temperature, an electron beam of monochromatic energy is made to impinge upon the sample, and the light emission is measured. Thereafter, the temperature of the temperature controller 22 is regulated to room temperature +50° C., and the crystal temperature of the filter 6 is elevated through the heat transfer member 24 and metal mesh 8. Then, with the crystal temperature of the filter 6 held at room temperature +50° C., the electron beam of monochromatic energy is made to impinge upon the sample, the resulting light emission is measured and the processor 18 computes the differential between the results of the two measurements. This makes it possible to measure the emission strength of a constant $h\nu$. In the description given above, the filter 6 is heated to make its temperature higher than room temperature. However, the filter 6 can instead by cooled to makes its temperature lower than room temperature, and the cutoff energy of the ionic crystal corresponding to this temperature also can be used. In addition, the temperature of the ionic crystal used in the two measurements can be made different temperatures other than room temperature by means of the temperature controller 22. As a result, it is possible to set the temperature of the ionic crystal and the cutoff energy corresponding thereto so that there will be no influence from room temperature.

The seventh embodiment shown in FIG. 10 is an arrangement in which the signal processing of the sixth embodiment is implemented in digital fashion. The method in which the filter 6 is used in this embodiment is the same as that described in connection with the sixth embodiment.

In the foregoing embodiments, a case is described in which a Cu-BeO photomultiplier is used as the vacuum ultraviolet-ray detector. However, a Geiger-Müller counter also can be employed as the detector of the inverse photoemission spectroscopic apparatus.

Further, a constant $\Delta E$ can be realized by adopting a mixed crystal of ionic crystals having different absorption edges.

According to the inverse photoemission spectroscopic apparatus of the present invention, the low-energy characteristic can be completely eliminated by adopting the differential between two ionic crystal filters having slightly different high-energy cutoff energies. As a result, the bandpass characteristic is decided by the sharp characteristic of high-energy cutoff. Accordingly, a bandpass characteristic having a narrower half-width $\Gamma$ can be realized by high-energy cutoff due to the exciton absorption band (full half-width $2\Gamma$) in the fundamental absorption edge of the ionic crystal.

Accordingly, in the inverse photoemission spectroscopic apparatus of the present invention, inverse photoemission spectroscopy of less than 9-11 eV can be achieved with no loss of light intensity.

In particular, if the ionic crystal is cooled to the temperature of liquid nitrogen and has the optimum thickness, an energy resolution of 0.1 eV can be achieved. If this degree of resolution can be realized, the spectrochemical analysis that can be achieved will compare favorably with other methods of spectrochemical analysis, and the range of application thereof will be very wide.

The present invention can be practiced in a variety of other forms without departing from the spirit and principal features thereof. Consequently, the above-described embodiments are merely simple examples in all aspects and are not to be interpreted in a restrictive manner. The scope of the invention is as indicated in the claims and is in no way restricted to the text of the specification. Furthermore, modifications and changes which fall within a scope equivalent to the scope of the claims are covered by the scope of the invention.

What is claimed is:

1. An apparatus for inverse photoemission spectroscopy for applying an electron beam to a sample and measuring light emitted from the sample, thereby detecting an unoccupied electronic state of the sample, comprising:
   (a) vacuum ultraviolet-ray detector; and
   (b) an optical filter provided in front of said detector, said optical filter selectively having at least two different cutoff energies.

2. The apparatus according to claim 1, wherein said optical filter comprises two ionic crystal filters having different cutoff energies.

3. The apparatus according to claim 2, wherein at least one of said two ionic-crystal filters is capable of being moved.

4. The apparatus according to claim 2, wherein the ionic-crystal filter having the larger cutoff energy is fixed in an optical path, and the ionic-crystal filter having the smaller cutoff energy is capable of being selectively moved into the optical path.

5. The apparatus according to claim 1, wherein said optical filter comprises an ionic-crystal filter having a cutoff energy which is temperature dependent.

6. The apparatus according to claim 5, wherein said ionic-crystal filter is capable of being moved.

7. The apparatus according to claim 5, further comprising temperature control means for setting the temperature of said ionic-crystal filter.

8. A method of inverse photoemission spectroscopy for applying an electron beam to a sample and measuring light emitted from the sample, thereby detecting an unoccupied electronic state of the sample, comprising the steps of:

(a) obtaining two outputs from a photodetector via optical filters having different cut-off energies;

(b) obtaining a differential between the two outputs; and (c) measuring the intensity of the emitted light based upon the differential between the two outputs.

9. The method according to claim 8, wherein the two outputs from the photodetector are obtained by selectively inserting, into an optical path, the optical filters having the different cutoff energies.

10. The method according to claim 8, wherein the optical filter having the larger cutoff energy is fixed in an optical path, and the optical filter having the smaller cutoff energy is capable of being selectively moved into the optical path.

* * * * *